(12) United States Patent
Pelc et al.

(10) Patent No.: US 7,062,006 B1
(45) Date of Patent: Jun. 13, 2006

(54) COMPUTED TOMOGRAPHY WITH INCREASED FIELD OF VIEW

(75) Inventors: Norbert J. Pelc, Los Altos, CA (US); Rebecca Fahrig, Palo Alto, CA (US); Edward G. Solomon, Menlo Park, CA (US)

(73) Assignees: The Board of Trustees of the Leland Stanford Junior University, Stanford, CA (US); Nova Ray, Palo Alto, CA (US)

( * ) Notice: Subject to any disclaimer, the term of this patent is extended or adjusted under 35 U.S.C. 154(b) by 0 days.

(21) Appl. No.: 11/039,716

(22) Filed: Jan. 19, 2005

(51) Int. Cl.
*G01N 23/00* (2006.01)

(52) U.S. Cl. .............................. 378/9; 378/19

(58) Field of Classification Search .................... 378/4, 378/9, 20, 21, 92, 193, 205
See application file for complete search history.

(56) References Cited

U.S. PATENT DOCUMENTS

| | | | | |
|---|---|---|---|---|
| 4,008,400 A * | 2/1977 | Brunnett et al. | ............... | 378/4 |
| 4,196,352 A | 4/1980 | Berninger et al. | ............. | 378/7 |
| 4,637,040 A * | 1/1987 | Sohval et al. | ................... | 378/9 |
| 4,670,657 A * | 6/1987 | Hawman et al. | ......... | 250/505.1 |
| 5,001,347 A | 3/1991 | Hsieh | ..................... | 250/363.1 |
| 5,173,852 A * | 12/1992 | Lonn | .............................. | 378/9 |
| 5,265,142 A * | 11/1993 | Hsieh | ............................. | 378/4 |
| 5,430,297 A | 7/1995 | Hawman | .................. | 250/363.1 |
| 5,825,842 A | 10/1998 | Taguchi | ....................... | 378/15 |
| 5,864,598 A | 1/1999 | Hsieh et al. | .................... | 378/4 |
| 5,966,422 A | 10/1999 | Dafni et al. | ................... | 378/9 |
| 6,229,870 B1 | 5/2001 | Morgan | ......................... | 378/9 |
| 6,389,097 B1 | 5/2002 | Bulkes et al. | ................. | 378/19 |
| 6,570,951 B1 | 5/2003 | Hsieh | ............................. | 378/4 |
| 6,654,440 B1 | 11/2003 | Hsieh | ............................. | 378/4 |
| 2003/0043957 A1 | 3/2003 | Pelc | ............................. | 378/4 |
| 2003/0043958 A1 | 3/2003 | Mihara et al. | ................. | 378/4 |
| 2005/0190878 A1* | 9/2005 | De Man et al. | ................ | 378/9 |

* cited by examiner

*Primary Examiner*—Edward J. Glick
*Assistant Examiner*—Anastasia Midkiff
(74) *Attorney, Agent, or Firm*—Lumen Intellectual Property Services Inc.

(57) ABSTRACT

A volumetric computed tomography system with a large field of view has, in a forward geometry implementation, multiple x-ray point sources emitting corresponding fan beams at a single detector array. The central ray of at least one of the fan beams is radially offset from the axis of rotation of the system by an offset distance D. Consequently, the diameter of the in-plane field of view provided by the fan beams may be larger than in a conventional CT scanner. Any number of point sources may be used. Analogous systems may be implemented with an inverse geometry so that a single source array emits multiple fan beams that converge upon corresponding detectors.

13 Claims, 4 Drawing Sheets

COMPUTED TOMOGRAPHY WITH INCREASED FIELD OF VIEW

FIELD OF THE INVENTION

The present invention relates generally to systems and methods for computed tomography. More specifically, it relates to improved techniques for increasing the field of view in computed tomography.

BACKGROUND OF THE INVENTION

In a conventional third-generation computed tomography (CT) system a single x-ray source 100 generates a fan beam 102 directed at an extended detector array 104, as shown in the cross-sectional view of FIG. 1. Fan beam 102 has a collection of rays diverging from source 100 at a divergence angle α, as shown. A system of this type, where the fan beam diverges from a single point source to a large array of detectors, is said to have a forward geometry. In an inverse geometry system, the, point source is exchanged for a small array of detectors (or a single detector) and detector array is exchanged for a source array, so that the set of measurement rays converge at the detectors. In the context of the present invention, forward and inverse geometry systems have similar geometrical properties. Thus, the common geometrical properties of both forward and inverse geometries can be described by considering just the forward geometry case.

The rays of the fan beam 102 include a central ray 108 which is defined to be the ray from the point source 100 that intersects a midpoint 110 of the detector array 104. (In the corresponding inverse geometry, the central ray is the ray from the midpoint of the source array to the mid-point of the small detector.) Note that in this conventional system the central ray 108 passes through (or very close to) a rotational axis 106 of the system. During operation of the system, source 100 and detector 104 are rotated around rotational axis 106 to various rotated positions. For example, FIG. 1 shows a rotated position corresponding to a rotation of the central ray 108 by an angle θ. As the source 100 and detector 104 rotate, fan beam 102 also rotates, providing the system with the capability to acquire x-ray transmission data at various angles from which an image is reconstructed. The rotational angles θ must cover a sufficient range so as to allow objects to be properly reconstructed. In this case, the range of θ values must be at least a plus 180 degrees. A field of view (FOV) 114 of the system is the region that is always exposed to the fan beam. Thus, for example, any portion of an object that is positioned within FOV 114 will be viewed from all rotational angles of the system. Outside of FOV 114, however, image data is not available at some rotational angles. As a result, CT systems are designed to reconstruct three-dimensional representations of objects within the FOV of the system. (Here the FOV is the in-plane FOV, i.e., the FOV within the cross-sectional plane of the fan beam which is perpendicular to the rotational axis.)

In the conventional CT system shown in FIG. 1 the size of FOV 114 is limited by the size of the detector array 104. In particular, the diameter of FOV 114 is always significantly less than the extent of the detector array. An increased FOV can be provided by increasing the size of the detector array, as shown in FIG. 2. A source 200 emits a fan beam 202 toward a larger detector array 204. Fan beam 202 has a central ray 208 which passes through (or very close to) rotational axis 206 and intersects a midpoint 210 of detector array 204. Due to the increased size of the detector array 204, the system has an increased FOV 214 as compared to the smaller FOV 212 provided by the smaller detector. (Similarly, an inverse geometry system also has an increased FOV if it has an increased source array size.) Although the FOV of a CT system can be increased using a larger detector array, increasing the size of the array often introduces significant technical difficulty and expense.

Another drawback of this CT system design is that the source and detector must rotate through a large angle to acquire images from a sufficiently large range of angles. If a patient moves during the rotation, the image data from different angles will not be consistent, resulting in artifacts and errors in the reconstructed three-dimensional representation. Alternative CT system designs (such as U.S. Pat. No. 5,966,422 to Dafni et al. and U.S. Pat. No. 4,196,352 to Berninger et al., which are incorporated herein by reference) have been proposed in an attempt to overcome this disadvantage. For example, FIG. 3 shows a CT system with multiple sources 300, 302, 304 and multiple corresponding detector arrays 306, 308, 310. The sources 300, 302, 304 emit corresponding fan beams 312, 314, 316 having respective central rays 318, 320, 322 all intersecting at a point coincident with (or very close to) an axis of rotation 324. Because the three source and detector pairs simultaneously provide image data at different angles, the required rotational angle is reduced by three, helping to mitigate problems caused by patient movement during scanning. However, the field of view 326 of this system suffers from the same problem as the conventional single source-detector system of FIG. 1. To increase the FOV of this system, the detector array sizes must be increased. In any case, the FOV is always less than the detector size. Moreover, despite the use of three detector arrays and sources, there is no FOV increase compared to the single source-detector system of FIG. 1. (The same disadvantages apply to the analogous inverse geometry system.)

An alternative CT system that provides a slight increase in FOV is shown in FIG. 4 (see also U.S. Pat. No. 5,430,297 to Hawman, which is incorporated herein by reference). A single source 400 emits a fan beam 402 directed at a detector array 404. A central ray 406 of fan beam 402 intersects a midpoint 410 of detector 404. In contrast to the conventional system of FIG. 1, however, the fan beam 402 of source 400 is offset from centerline 412 so that the central ray 406 is offset from the rotational axis 408 of the system. Consequently, line 418 from source 400 passing through axis 408 intersects the detector 404 at a point 420 that is far from midpoint 410. As the source 400 and detector 404 rotate around rotational axis 408, the single fan beam also rotates around axis 408. Due to the offset of the fan beam, the FOV 414 of this system is larger than the FOV 416 of a comparable system with no offset, provided the system rotates through at least 360 degrees. The FOV 414, however, while larger than FOV 416, is still substantially limited unless the detector array is quite large. In particular, the diameter of the FOV of this system is always less than twice that of the system of FIG. 1, and generally less than the extent of the detector array. Moreover, the asymmetry of the system geometry requires a rotation of at least 360 degrees, introduces complexities to the data processing required to reconstruct a representation of the object from the data collected at various angles, and in general has non-uniform noise behavior. (The analogous inverted system has similar limitations.)

SUMMARY OF THE INVENTION

The present invention provides improved CT systems and methods that enjoy substantially increased FOV. The diameter of the in-plane FOV of CT systems according to the present invention can be larger than the in-plane extent of the detector (or source) array. Thus, the invention provides CT systems with increased FOV without the expense and complication of larger detector (or source) array sizes required in the past.

According to one aspect of the invention, a method is provided for volumetric computed tomography. In a forward-geometry implementation, multiple x-ray point sources emit corresponding fan beams at a single detector array at different corresponding times. X-ray image data is acquired at the detector array as the x-ray point sources and the detector are both rotated together around a rotational axis. Each of the fan beams has a central ray passing from the source to the midpoint of the detector. Thus, the central rays of at least two fan beams intersect at the detector midpoint, and the central ray of at least one fan beam is offset from the rotational axis by an offset distance. The diameter of the in-plane field of view provided by the combination of the fan beams is preferably larger than an in-plane extent of the detector array.

In some embodiments there are two sources, where at least one source has a fan beam whose central ray is offset from the rotational axis. The other source has a fan beam whose central ray may pass through the rotational axis (i.e., have no offset) or may be offset from the rotational axis.

In other embodiments, there are three or more sources, where at least one source has a fan beam whose central ray is offset from the rotational axis. The other sources have fan beams whose central rays may pass through the rotational axis or may be offset from the rotational axis. Additional embodiments include inverse geometry analogues and generalizations of the principles to 3D systems.

DETAILED DESCRIPTION

Figure 5:
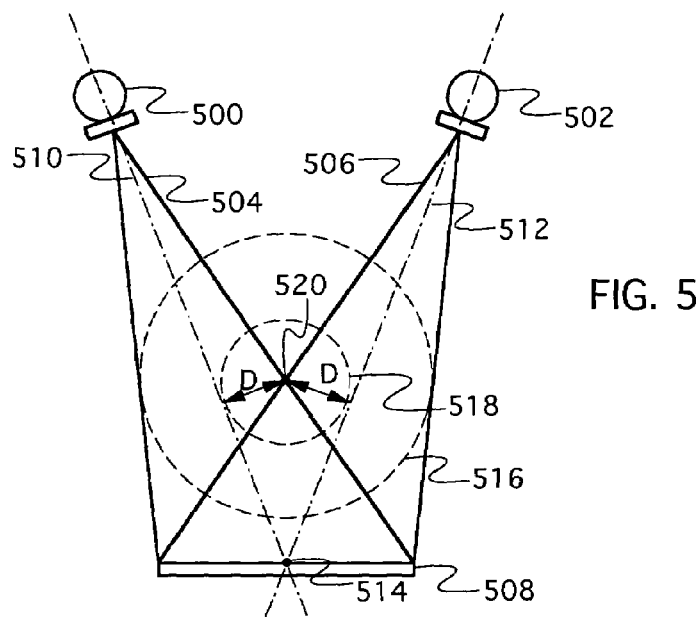
FIG. 5 is a cross-sectional illustration of a CT system having two sources whose fan beams are both offset from the system's rotational axis according to an embodiment of the present invention.

A volumetric CT system according to one embodiment of the invention is illustrated in FIG. 5. Two x-ray point sources 500 and 502 emit corresponding fan beams 504 and 506 at a single detector array 508 at different corresponding times. X-ray image data is acquired from the detector array 508 to reconstruct a representation of an object of interest. The x-ray point sources 500 and 502, as well as the detector 508 are rotated together around a rotational axis 520 of the system. Consequently, fan beams 504 and 506 also rotate about axis 520. The fan beams 504 and 506 have corresponding central rays 510 and 512 that bisect the detector array 508 at a midpoint 514. Because the multiple fan beams are directed toward a common detector array from sources having different locations, the central rays 510 and 512 have different angular orientations and are radially offset from the rotational axis 520 by a significant offset distance D, resulting in a FOV 516 for the system which is significantly larger than the limited FOV 518 of prior systems. There are prior art systems that employ a technique called "focal-spot wobbling" to improve in-plane sampling and reduce certain artifacts. In these systems, the focal spot is rapidly moved a short distance, causing a displacement of the central ray of less than 1% of the FOV of a single centered fan beam. With respect to the present invention, the displacement caused by focal spot wobbling is not significant. The offset distance D of a fan beam is considered significant when it is approximately equal to or larger than 25%, and preferably on the order of 50% for the system of FIG. 5, of the width of the fan beam near the rotational axis. Moreover, the diameter of the in-plane field of view provided by the fan beams of this system can be larger than an in-plane extent of the detector array 508. In prior systems, the FOV is smaller than the size of the detector array.

Figure 6:
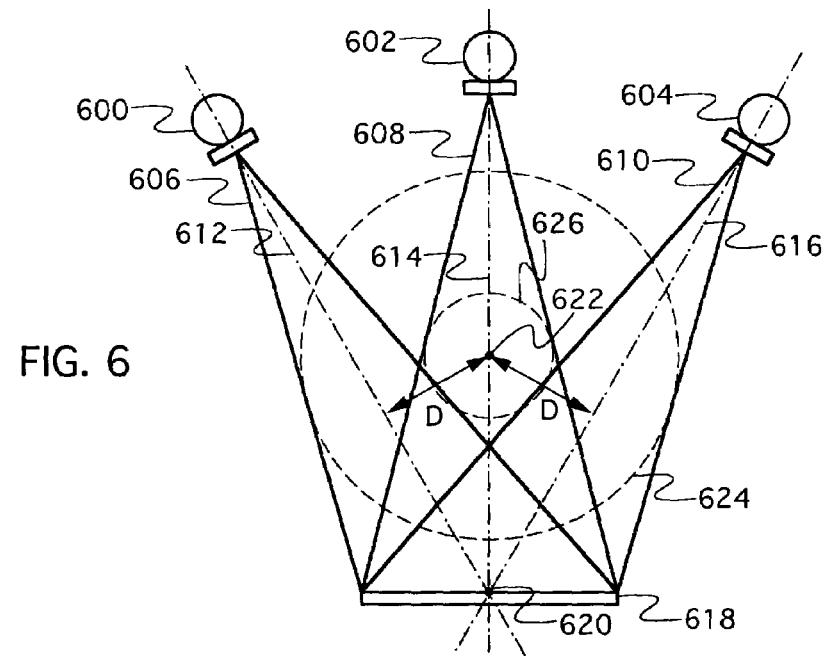
FIG. 6 is a cross-sectional illustration of a CT system having three sources, where two of the three fan beams are offset from the system's rotational axis according to an embodiment of the present invention.

Another embodiment of the invention is illustrated in FIG. 6. Three x-ray point sources 600, 602, 604 emit three respective fan beams 606, 608, 610 directed at a single detector array 618. Because a single detector is used with multiple sources, the sources emit their corresponding beams at different corresponding times. Fan beams 606, 608, 610 have three respective central rays 612, 614, 616 with different angular orientations. Although central ray 614 of beam 608 passes through rotational axis 622, central rays 612 and 616 of beams 606 and 610, respectively, are offset from rotational axis 622 by an offset distance D. Central rays 612, 614, 616 intersect the detector array 618 at a midpoint 620. Due to the novel design, FOV 624 can be significantly larger even than the extent of the detector array 618. As evident from the figure, the FOV 624 is nearly three times larger than the FOV 626 of a prior art CT system. To obtain a FOV of comparable size, the prior art CT system would require a significantly larger detector array, increasing the expense and complexity of the system.

In another embodiment of the invention, the system of FIG. 6 is modified by eliminating source 604, which yields a system in which fan beam 608 has a central ray that passes through the rotational axis 622, while fan beam 606 has a central ray that is offset from the rotational axis 622. Thus, at least one of the two fan beams (i.e., in this case beam 606) has a central ray that is offset. The FOV 624 for this embodiment is larger than that of the embodiment described above in relation to FIG. 5 even though they both use the same size detector array and fan beam. In addition, the edges of the fan beams in this system do not intersect at the rotational axis as they do in the system of FIG. 5, avoiding problems with discontinuities there. Note, however, that this embodiment with only two fan beams requires a 360 degree rotation to obtain the maximum FOV.

Figure 1:
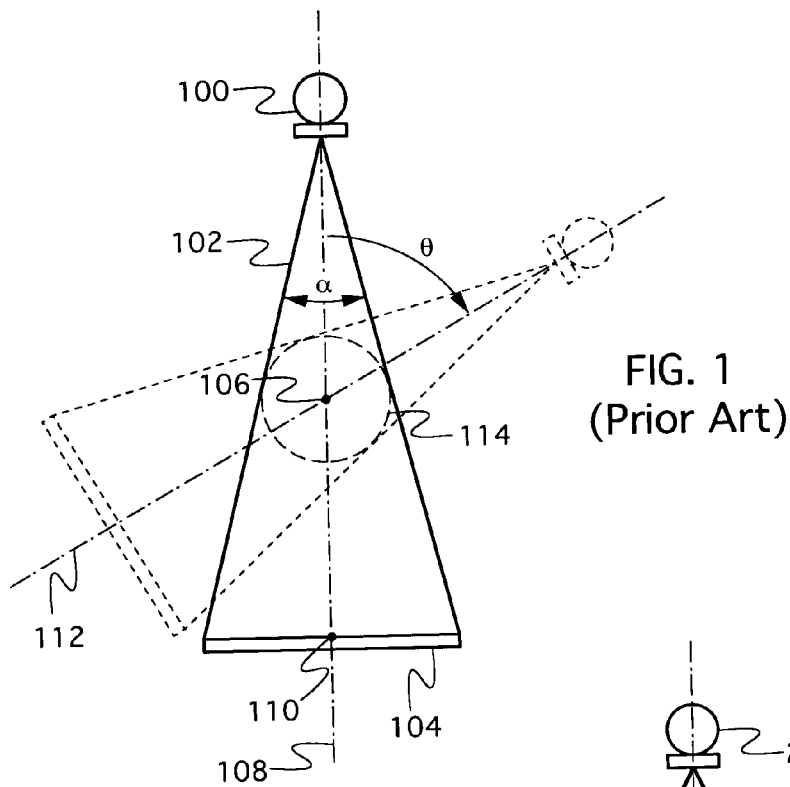
FIG. 1 is a cross-sectional illustration of a conventional CT system having an x-ray point source emitting a fan beam toward a detector array.
Figure 2:
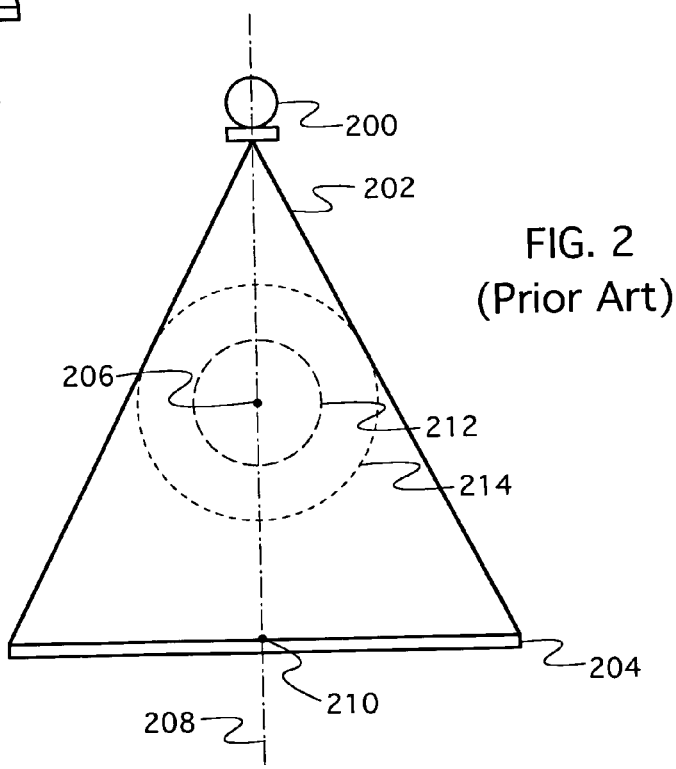
FIG. 2 is a cross-sectional illustration of a conventional CT system similar to the system of FIG. 1 except with a larger detector array to provide an increased field of view.
Figure 3:
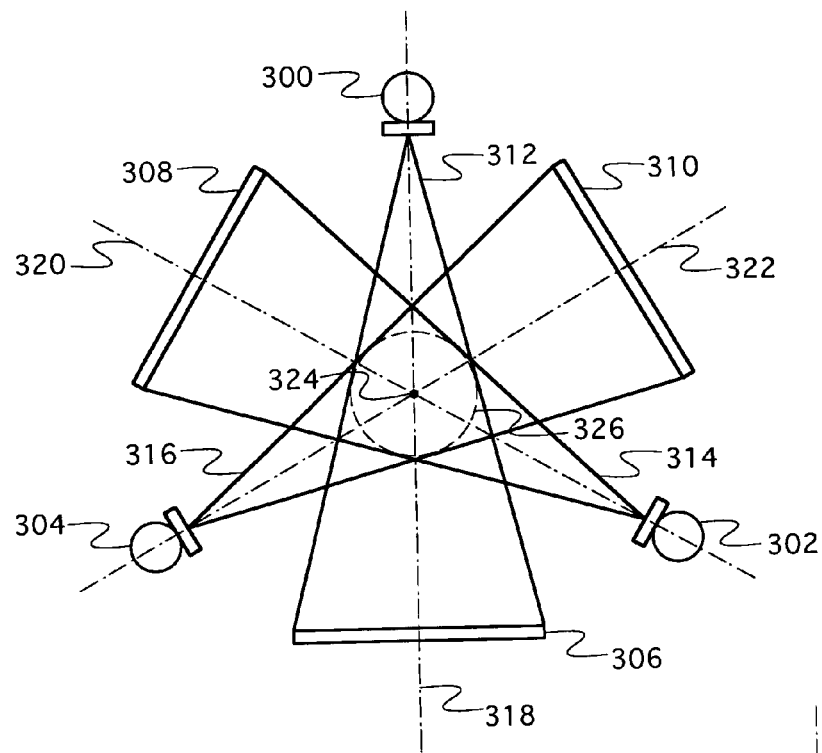
FIG. 3 is a cross-sectional illustration of a known CT system similar to that of FIG. 1 except with multiple sources and multiple corresponding detector arrays providing more efficient scanning, but no increase in field of view.
Figure 4:
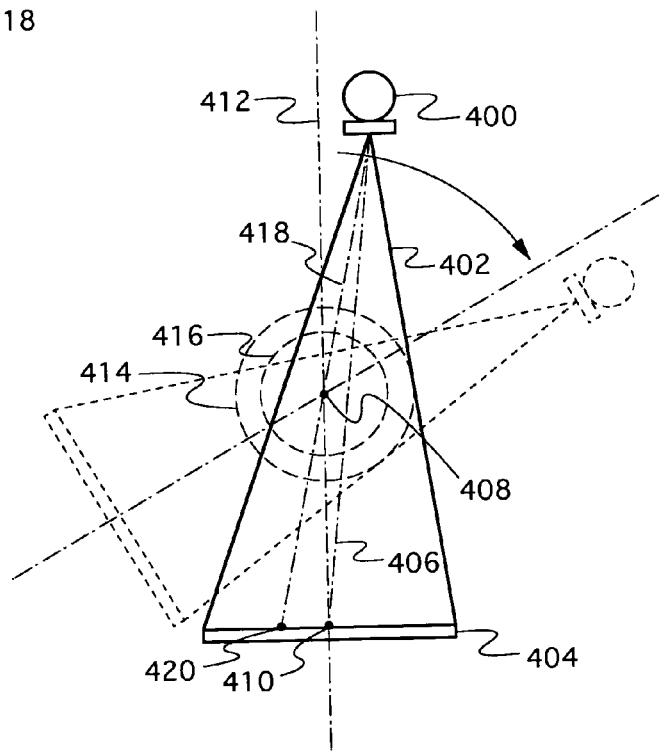
FIG. 4 is a cross-sectional illustration of a known CT system similar to that of FIG. 1 except with the single source offset a small distance off axis, providing up to a factor of two increase in field of view.
Figure 7:
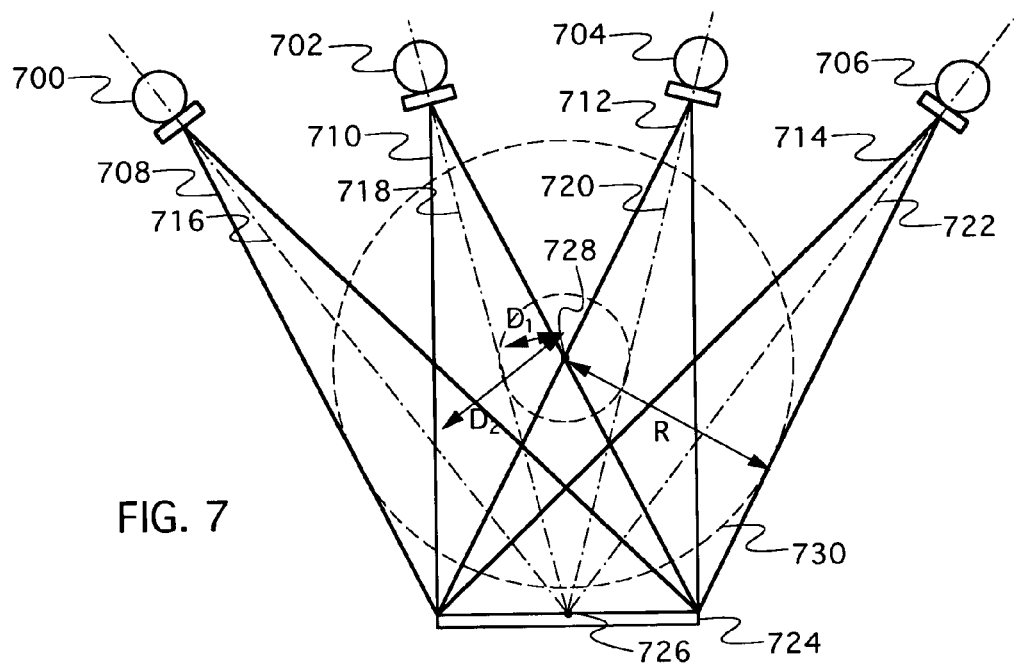
FIG. 7 is a cross-sectional illustration of a CT system having four sources whose fan beams are all offset from the system's rotational axis according to an embodiment of the present invention.

In yet another embodiment of the invention, four sources 700, 702, 704, 706 emit four respective fan beams 708, 710, 712, 714 directed at a single detector array 724, as shown in FIG. 7. Fan beams 708, 710, 712, 714 have respective central rays 716, 718, 720, 722 which intersect detector 724 at a midpoint 726 and are offset from the rotational axis 728 by offset distances $D_1$ (for central rays 718 and 720) and $D_2$ (for central rays 716 and 722). Note that the diameter of FOV 730 is almost twice as large as the extent of detector array 724. In contrast, prior art systems such as that shown in FIG. 1 have a FOV diameter on the order of half the size of the detector array.

In an alternate embodiment, the system of FIG. 7 is modified by eliminating either one or both of the sources 704 and 706. The system still will have multiple sources, at least one of which has a fan beam whose central ray is offset from the axis of rotation. Elimination of sources, however, may require increased rotation of the system to acquire sufficient data.

The system of FIG. 7 can also be modified by adding still more sources, providing a further increase in the FOV of the system. Although providing multiple offset sources increases the FOV, the greatest FOV increase per additional source is obtained when there are fewer sources. Thus, it is preferred that the number of sources is an integer from two to ten. Although not necessary, it is most preferred to have an odd number of sources, where one of the sources has a fan beam whose central ray passes through the rotational axis and all the other sources have fan beams whose central rays are offset from the rotational axis. An odd number of sources is preferred over an even number of sources in order to avoid sampling discontinuities at the center of rotation where edges of two innermost fan beams may intersect. It is possible, however, for a system with an even number of sources to avoid this problem by increasing the overlap between the two innermost fan beams, i.e., slightly decreasing the displacements of their central rays from the rotational axis.

The offsets of the central rays of the fan beams provide the system with a diversity of radial samples. In embodiments where N fan beams are symmetrically placed about the center of rotation and are uniformly spaced, the rays in one fan preferably have offset distances from the rotational axis that differ from the offset distances of the rays in an adjacent fan beam by approximately 2R/N, where R is the radius of the FOV. In other embodiments, however, the rays in the fan beams are not necessarily offset uniformly.

It should also be noted that in alternate embodiments the distances from the sources to the detector array may be different from each other. In addition, the distances from the sources to the axis of rotation may be different from each other.

Figure 8:
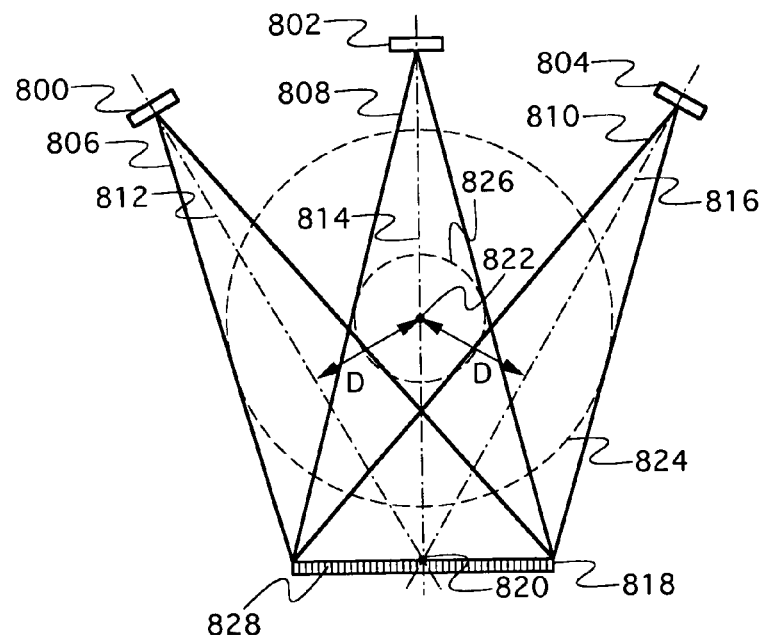
FIG. 8 is a cross-sectional illustration of an inverse geometry CT system having one source array and two detectors, wherein the two corresponding fan beams are offset from the system's rotational axis according to an embodiment of the present invention.

In view of the above description, those skilled in the art will appreciate that various inverse geometry systems analogous to the systems described above may be provided by replacing the multiple point sources with multiple small detectors (e.g., small detector arrays) and replacing the detector array with a source array whose collimators provide x-rays directed at the multiple detectors. (Examples of inverse geometry systems can be seen in US Patent Application Publication 20030043957 to Pelc and US Patent Application Publication 20030043958 to Mihara et al., which are incorporated herein by reference.) For example, a preferred embodiment of the present invention having an inverse geometry is shown in FIG. 8. A single source array 818 is comprised of a large number of source locations, each with its own collimator within the collimator array 828. The collimators in 828 are designed to limit the x-rays so that they are directed at the three detectors 800, 802, 804. For example, each collimator may be designed to simultaneously illuminate all three detector arrays. An alternative collimator design is to dedicate each source position and corresponding collimator to direct x-rays to just one of the detector arrays, alternating adjacent collimators between the three detectors. In one implementation, the source array has 100 source positions in the lateral direction, separated from each other by 2.5 mm, and the detector has 50 detector elements in the lateral dimension, separated from each other by about 1 mm. The net effect of the source array 818 is to produce three fan beams 806, 808, 810 directing x-rays to converge upon three corresponding detectors 800, 802, 804. As in the forward geometry system, each fan beam 806, 808, 810 has a corresponding central ray 812, 814, 816 that is defined as the line connecting the midpoint 820 of the source array to the center of the corresponding detector array 800, 802, 804. A conventional inverted fan beam system has a single detector 802 and corresponding inverted fan 808 which determines the limited FOV 826. In contrast, the present embodiment has additional detectors 800, 804 and corresponding fan beams 806, 810 providing increased FOV 824. Fan beams 806, 810 have respective central rays 812 and 816 which are both offset from the axis of rotation 822 by radial distance D. More generally, note that each of the three inverted fan beams has a set of rays, each having a radial offset distance from the axis of rotation, the central ray providing one example of such a ray and its offset distance D. Ideally, the radial distances for the rays in all the beams are selected so as to have these three sets of radial distances overlapping slightly. Moreover, ideally the distribution of radial distances from all the fan beams should be relatively smooth and relatively uniform. The set of radial distances sampled by the set of three detector arrays produces FOV 824.

In the forward as well as the inverse geometry embodiments described above, the FOV has been described as a two dimensional field of view. As will be clear to one of skill in the art, the present invention is also useful in volumetric or 3D systems. (Examples of various known 3D CT systems are disclosed in US Patent Application Publication 20030043957 to Pelc, U.S. Pat. No. 6,229,870 to Morgan, U.S. Pat. No. 6,654,440 to Hsieh and U.S. Pat. No. 5,966, 422 to Dafni et al., which are incorporated herein by reference.) For example, the systems of FIGS. 5, 6, and 7 could be modified so that the detector is a 2-dimensional detector and the fan beams are cone beams. In one rotation of the gantry, the systems would be able to collect data to reconstruct a 3D volume, wherein the present invention is being used to increase the field of view in the trans-axial direction (i.e., in the plane of the drawings). Similarly, the system of FIG. 8 could be a volumetric CT scanner if the source array is a 2D array, having an extent into the plane of the drawing, and each detector array is a 2D array having an extent into the plane of the drawing. In a preferred embodiment of this latter system the extents of the source and detector arrays into the plane of the drawing are approximately the same.

In operation, the systems described above are used in a manner similar to conventional CT systems. Thus, an object of interest is placed within the FOV of the system and x-ray projection data are acquired at various rotational angles. The projection data is then processed by a computer to produce representations (e.g., images) of the object which may be displayed for viewing by a radiologist in the case of medical diagnostic applications. The systems could also be used for other applications, such as non-destructive testing or baggage inspection.

The reconstruction algorithms used in CT systems for processing projection data (e.g., see U.S. Pat. No. 5,825,842 to Taguchi, which is incorporated herein by reference) may be adapted to operate with systems employing the principles of the present invention. For the inverse geometry system, one possible reconstruction algorithm re-bins the data into parallel ray projections, with the data from all the detector arrays being used together in the re-binning. Forward geometry systems would process data analogously, re-binning the data into parallel ray projections.

The present invention also provides the possibility for other modified reconstruction techniques. For example, in a system such as shown in FIG. 5, 6, or 7, consider the case where two fan beams are produced by two sources that are positioned at the same distance from the axis of rotation (e.g., fan beam pair 504 and 506 in FIG. 5) and are mounted with an angle δ between them, so that after the gantry rotates by an angle δ the second source is at the same location that the first source was in prior to the rotation. As a result, the fan beam data produced by the first source at gantry angle θ can be combined with the data produced by the second source at gantry angle θ+δ to produce a larger fan beam for reconstruction. Extensions and variations of this approach for the systems of FIG. 6 or 7, or for inverse geometry systems, will be evident to those skilled in the art.

The invention claimed is:

1. A computed tomography system comprising:
   multiple x-ray detectors;
   a source array for generating corresponding fan beams directed at the detectors;
   wherein the x-ray source array and the detectors are capable of being rotated together around a rotational axis; and
   wherein the fan beams have corresponding central rays connecting the corresponding detectors to a midpoint of the source array, wherein the central ray of at least one of the fan beams is offset from the rotational axis by a substantial offset distance D.

2. The system of claim 1 wherein the source array comprises a set of collimators, wherein each collimator simultaneously directs x-rays toward the multiple detectors.

3. The system of claim 1 wherein the source array comprises a set of collimators arranged to alternate adjacent collimators between different types, wherein each type of collimator directs x-rays toward one of the multiple detectors.

4. The system of claim 1 wherein the fan beams have corresponding sets of rays, each ray having a radial offset distance from the rotational axis, wherein the radial offset distances of the rays in the sets are selected such that there is an overlap of radial offset distances between the sets.

5. The system of claim 1 wherein at least one of the fan beams has a central ray that is radially offset from the rotational axis by a distance D approximately equal to or greater than a width of the corresponding fan beam near the rotational axis.

6. The system of claim 1 wherein rays in one of the fan beams have offset distances from the rotational axis that differ from offset distances of rays in an adjacent one of the fan beams by approximately 2R/N, where R is a radius of a field of view provided by the fan beams and N is the number of point sources.

7. A method of computed tomography comprising:
   providing multiple x-ray detectors and a source array;
   emitting from the source array corresponding fan beams directed at the detectors;
   acquiring x-ray data at the detectors; and
   rotating the x-ray detectors and the source array around a rotational axis;
   wherein the fan beams have corresponding central rays connecting the corresponding detectors to a midpoint of the source array, wherein the central ray of at least one of the fan beams is offset from the rotational axis by a substantial offset distance D.

8. The method of claim 7 wherein the fan beams have corresponding sets of rays, each ray having a radial offset distance from the rotational axis, wherein the radial offset distances of the rays in the sets are selected such that there is an overlap of radial offset distances between the sets.

9. The method of claim 7 wherein at least one of the fan beams has a central ray that is radially offset from the rotational axis by a distance D approximately equal to or greater than a width of the corresponding fan beam near the rotational axis.

10. The method of claim 7 wherein a diameter of a field of view provided by the fan beams is larger than an extent of the source array.

11. The method of claim 7 wherein none of the central rays passes through the rotational axis.

12. The method of claim 7 wherein the central rays all intersect at a midpoint of the source array.

13. The method of claim 7 wherein rays in one of the fan beams have offset distances from the rotational axis that differ from offset distances of rays in an adjacent one of the fan beams by approximately 2R/N, where R is a radius of a field of view provided by the fan beams and N is the number of point sources.

* * * * *